United States Patent [19]
Grote et al.

[11] Patent Number: 6,162,623
[45] Date of Patent: *Dec. 19, 2000

[54] PROCESSES FOR PREPARING AND USING IMMOBILIZED LIPASES

[75] Inventors: Martin Roger Grote, Rotterdam; Johan Paul Geurtsen, Maassluis; Karel Petrus Van Putte, Maasland, all of Netherlands

[73] Assignee: Lipton, division of Conopco, Inc., Englewood Cliffs, N.J.

[ * ] Notice: This patent is subject to a terminal disclaimer.

[21] Appl. No.: 08/983,085

[22] PCT Filed: Jun. 14, 1996

[86] PCT No.: PCT/EP96/02587

§ 371 Date: Dec. 29, 1997

§ 102(e) Date: Dec. 29, 1997

[87] PCT Pub. No.: WO97/01632

PCT Pub. Date: Jan. 16, 1997

[30] Foreign Application Priority Data

Jun. 27, 1995 [EP] European Pat. Off. .............. 95201738

[51] Int. Cl.[7] .............. C12P 7/64; C12N 11/02; C12N 11/10; C12N 11/12
[52] U.S. Cl. .......... 435/134; 435/177; 435/178; 435/179
[58] Field of Search ................. 435/134, 174, 435/176, 177, 178, 179

[56] References Cited

U.S. PATENT DOCUMENTS

| | | | |
|---|---|---|---|
| 4,275,011 | 6/1981 | Tanaka et al. | 260/410.7 |
| 5,182,201 | 1/1993 | Tauda | 435/176 |
| 5,316,927 | 5/1994 | Zaks et al. | 435/134 |
| 5,330,905 | 7/1994 | Kula et al. | 435/183 |
| 6,025,171 | 2/2000 | Fabian et al. | 435/134 |

FOREIGN PATENT DOCUMENTS

| | | |
|---|---|---|
| 035 883 | 9/1981 | European Pat. Off. . |
| 140 542 | 5/1985 | European Pat. Off. . |
| 320 132 | 6/1989 | European Pat. Off. . |
| 382 767 | 8/1990 | European Pat. Off. . |
| 407 058 | 1/1991 | European Pat. Off. . |
| 513 709 | 11/1992 | European Pat. Off. . |
| 444 092 | 7/1993 | European Pat. Off. . |
| 5344897 | 12/1993 | Japan . |
| 2159527 | 12/1985 | United Kingdom . |
| 89/01032 | 2/1989 | WIPO . |
| 95/22606 | 8/1995 | WIPO . |

*Primary Examiner*—David M. Naff
*Attorney, Agent, or Firm*—Gerard J. McGowan, Jr.

[57] ABSTRACT

An amphiphilic enzyme is immobilized by preparing an emulsion containing a continuous hydrophobic phase and a dispersed aqueous phase containing the enzyme and a carrier for the enzyme, and removing water from the dispersed phase until this phase turns into solid enzyme coated particles. The enzyme is preferably a lipase, and the immobilized lipase can be used for reactions catalyzed by lipase such as interesterification of mono-, di- or triglycerides, de-acidification of a triglyceride oil, or removal of phospholipids from a triglyceride oil when the lipase is a phospholipase. The aqueous phase may contain a fermentation liquid, an edible triglyceride oil may be the hydrophobic phase, and carriers include sugars, starch, dextran, water soluble cellulose derivatives and fermentation residues. A substance to be processed such as triglycerides, diglycerides, monoglycerides, glycerol, phospholipids or fatty acids may be in the hydrophobic phase.

12 Claims, 2 Drawing Sheets under United States

PROCESSES FOR PREPARING AND USING IMMOBILIZED LIPASES

The present invention relates to a process for the immobilization of enzymes and the use of the immobilized enzymes for catalyzing the processing of triglyceride fats.

BACKGROUND OF THE INVENTION

Enzymes are used on an industrial scale as catalysts for processing various crude materials. Often these processes are cost-effective only when the enzymes can be re-used many times. For recirculation the enzymes need to be separated from the process liquid. This is possible when the enzymes are attached to a carrier which can be filtrated or centrifuged.

An important group of industrial enzymes have an amphiphilic nature. Lipases and phospholipases belong to this group of enzymes, which are characterized by the presence of a hydrophilic part as well as a hydrophobic part in the molecule. Such enzymes, when dispersed in an emulsion, will migrate and accumulate in the interface of the aqueous and the oil phase. The hydrophobic part of the enzyme points into the hydrophobic phase and the hydrophilic part points into the aqueous phase.

The invention will be described with lipase as an example of an amphiphilic enzyme. Another industrially important amphiphilic enzyme is phospholipase of which various types are known and which is used for the hydrolysis of phospholipids to lysophospholipids. An industrial application is the enzymatic degumming of triglyceride oils, which is described in e.g. EP 513 709.

Lipases are employed for their ability to modify the structure and composition of triglyceride oils and fats. They catalyze different types of triglyceride conversions, such as hydrolysis, esterification and transesterification. These are equilibrium reactions which in one direction result into hydrolysis of triglycerides into free fatty acids and glycerol, mono- or diglycerides, and in the other direction result into re-esterification of glycerol, monoglycerides and diglycerides into triglycerides. For the re-esterification process removal of the water in the reaction medium is necessary to shift the equilibrium in the direction of the triglyceride synthesis.

The use of lipase in substantially water-free process media is associated with a major problem which is the solubilization of lipase in oil. For that purpose preferably a lipase is used which is active in a water-free environment and which is immobilized.

Presently the main process for lipase manufacture is a microbiological fermentation of suitable microorganisms which produce the enzyme under proper conditions. To a purified lipase solution a carrier is added and the enzyme is allowed to get attached to the carrier surface. Such immobilization method is exemplified for an interesterification process in e.g. GB 2 159 527. The attachment of the enzyme to the carrier enables easy separation of the irreversibly immobilized enzyme from the process medium for subsequent use.

Generally, the used carrier materials are porous, particulate, but always water insoluble materials which provide large surface areas per unit volume are. The preparation of immobilized enzymes is described in e.g. EP 0 140 542, EP 0 382 767, WO 95/22606, EP 0 444 092 and WO 89/01032.

Since the present immobilisation techniques require pure enzyme, the crude fermentation broth has to be subjected to an extensive and costly purification process which is a disadvantage inherent to the present production of immobilised enzyme systems.

Moreover, to the extent that the active parts of the immobilized enzyme are facing the carrier material rather than being exposed to the substrate, the activity will be correspondingly low. In the usual porous carrier materials mass transfer effects further limit the lipase activity.

The present invention aims to provide a process for immobilizing an enzyme in which a non-purified enzyme preparation may be utilized. Furthermore the present invention aims to provide a highly active, immobilized enzyme preparation which can be regenerated and reactivated.

SUMMARY OF THE INVENTION

The invention provides a process for the immobilization of an enzyme, characterized by the steps comprising a. selecting an amphiphilic enzyme for immobilization, b. preparing an emulsion comprising a continuous hydrophobic phase and a dispersed aqueous phase in which aqueous phase are dissolved the enzyme and material suitable to act as carrier for the enzyme when the next step is carried out, c. removing water from the dispersed phase until this phase turns into solid enzyme coated particles.

The invention further provides an amphiphilic enzyme which is immobilized by attachment to a particulate carrier which is soluble in an aqueous phase. The invention also provides processes in which this enzyme is employed.

Figure 1:
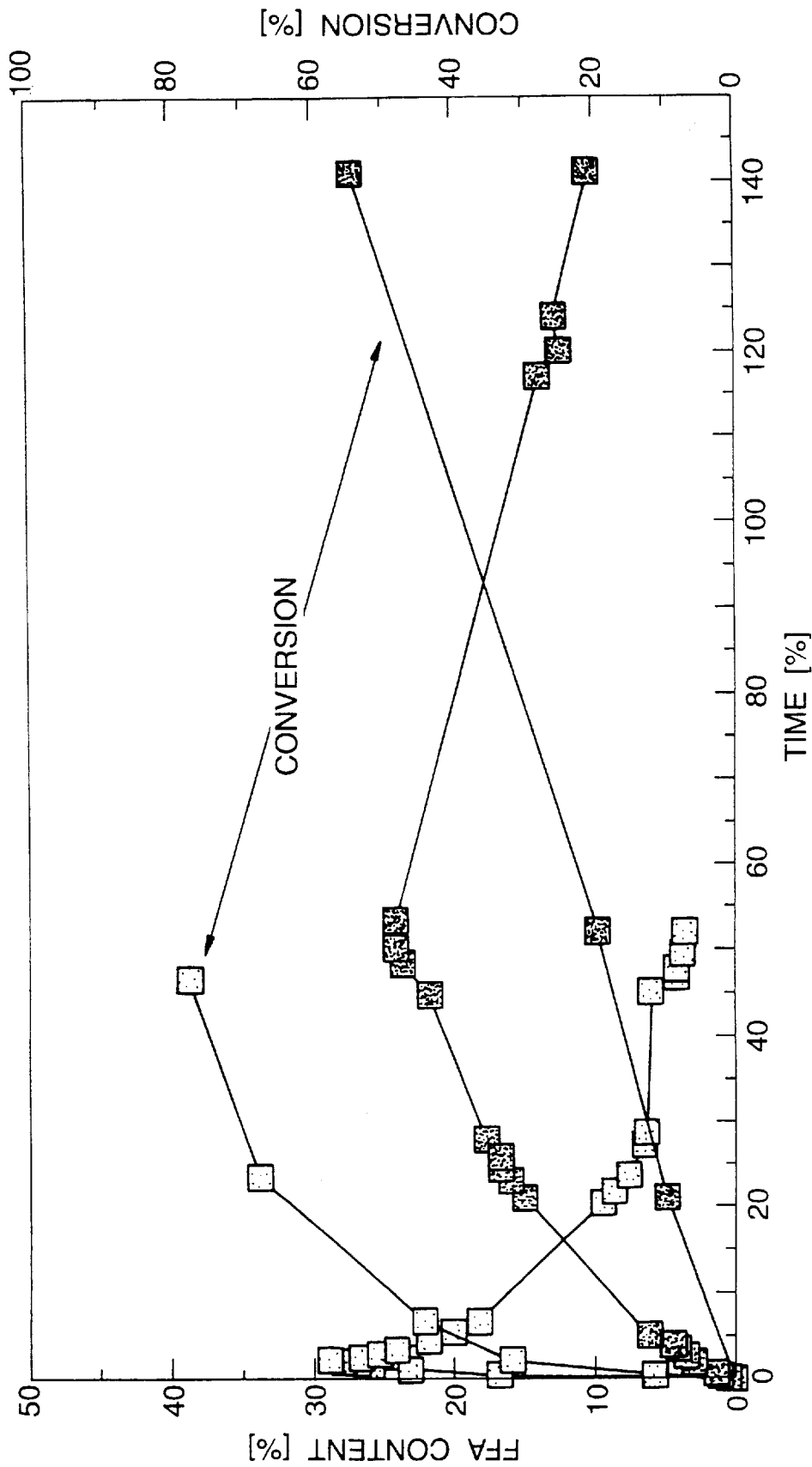
FIG. 1 shows the reaction course of the interesterification of a mixture of medium chain triglycerides and high oleic sunflower oil in the presence of an immobilized lipase. The free-fatty acid content and the conversion degree for a process using lipase (Lypozyme™) traditionally immobilized on Duolite™ (lines with heavy dots) is indicated as well as the free-fatty acid content and the conversion degree for a process using lipase (Lypozyme™ 10000 L) which is in-situ immobilized according to the present invention (lines with light dots).

For the 24 hours batches of the dark shaded areas the employed lipase is first immobilized according to the invention. The process reaction is a high oleic sunflower oil/medium chain triglyceride interesterification carried out at 35° C. For the 8 hours, 15 hours and weekend batches of the other (light grey) areas the immobilised lipase is used for POs/PKs interesterification at 60° C. in a "dry" form as separated by centrifuging from the preceding interesterification batch,

DETAILS OF THE INVENTION

The starting emulsion is prepared with, preferably, 5–10 wt. % of aqueous phase. The aqueous phase should contain the amphiphilic enzyme to be immobilized and further dissolved material which can act as carrier after it has been turned into solid matter. The aqueous phase preferably is a fermentation liquid still containing fermentation residues. This fermentation liquid preferably is the liquid in which the enzyme has been formed. Alternatively a solution of more or less purified enzyme may be used as aqueous phase. A major advantage of the present invention is that a preceding recovery and purification of the enzyme from the fermentation liquid is not required.

The carrier material is water soluble and is selected preferably from the group consisting of sugars, starch, such as wheaten flour, dextran, water soluble cellulose derivatives and fermentation residues. If not already present in the aqueous phase, the carrier material is added to the aqueous phase before or after it has been dispersed into the hydrophobic continuous phase. This addition is essential when the aqueous phase does not contain sufficient carrier material. Such addition may be supplemental to other carrier materials, e.g. fermentation residues already present.

The carrier material is present preferably in an amount of 0.5–5 wt. %, more preferably 1–2 wt. % on oil. Soluble means that the carrier substance when used in said amounts fully dissolves in the aqueous phase.

With fermentation residues are meant all substances still present in the supernatant: the enzyme fermentation liquid after the water insoluble matter including the biomass has been separated e.g. by centrifugation. Optionally, this supernatant is concentrated, e.g. by passing it through a crossflow hollow fibre microfiltration membrane module (known as artificial kidney). The fermentation residues comprise polysaccharides, proteinaceous material, salts and sugars. These substances are soluble in the aqueous fermentation liquid but separate as solid, particulate matter when the water is removed.

The aqueous enzyme containing phase is dispersed by usual emulsifying techniques as fine droplets in the hydrophobic phase. The amphiphilic enzyme migrates to and accumulates in the interface of both phases.

Any lipase suitable for triglyceride hydrolysis or re-esterification may be used, but preferably, the lipase is obtained from *Rhizomucor miehei, Humicola lanuginosa* or *Rhizopus niveus* fermentation. The amount of added enzyme activity is adapted to a particular process. Generally, a suitable lipase activity is 165 LU per gram oil.

The hydrophobic phase of the emulsion may be any food-grade liquid in which the aqueous phase can be dispersed. It may be, for example, hexane or, preferably, an edible triglyceride oil. If a triglyceride oil is used, preferably an oil is chosen which is substantially phospholipids free, otherwise the phospholipids may adversely interfere with the formation of the enzyme coated particles. Preferably the triglyceride oil contains not more than 100 ppm of hydratable phospholipids.

For the removal of water from the emulsion standard techniques are available including the addition of molecular sieves and conducting nitrogen through the emulsion, but drying is best accomplished by gradual evaporation of water, preferably applying a vacuum of 1–100 mbar, preferably 3–25 mbar or by a combination of such measures.

By removing the water from the dispersed aqueous phase, the droplets shrink and get desiccated. In the first instance dissolved carrier material, e.g. fermentation residues, will separate as solid particulate matter and finally the enzyme accumulated in the interface will deposit on and get attached to the solid particulate matter. In this way desiccation of the dispersed phase provides an in-situ immobilized enzyme preparation, which further distinguishes from prior art immobilized enzymes in that the enzyme is not irreversibly bound to the carrier. The enzyme may either be used as soon as immobilized, provided its substrate is present in or will be added to the hydrophobic phase or the enzyme may be separated and stored for future use.

Since the hydrophobic part of the enzyme with the active site remains during removal of the water oriented to a direction opposite the carrier surface, in the final immobilized enzyme the maximum number of active enzyme sites is available for catalysis.

Depending on the amount of enzyme in the aqueous phase the solid particles will be coated fully or partially with enzyme.

Preferably the hydrophobic phase either contains or consists of the substance to be processed and—for lipases and phospholipases—is selected from the group containing triglycerides, diglycerides, monoglycerides, glycerol, phospholipids and fatty acids.

As soon as a lipase containing W/O-emulsion has been formed, glyceride molecules, when present, start to be hydrolyzed into fatty acids and diglycerides, monoglycerides and glycerol. The hydrolysis, preferably in a stirred vessel, is continued until the hydrolysis attains a chosen level. As soon as in the next reaction step water is removed from the process mixture, the hydrolysis turns into a re-esterification process. A low FFA content of even 4 wt. % can be easily attained.

The present invention further relates to immobilized amphiphilic enzymes which are attached to a particulate carrier of which the carrier substance is soluble in an aqueous phase.

Enzymes immobilized according to the present invention are very active compared to similar prior art systems. The method of immobilization may have contributed to this high activity. When the immobilized enzyme is a lipase, it may be used at elevated temperatures without getting deactivated, provided the enzyme acts in a non-aqueous environment. Depending on the type of lipase, temperatures of 60° C. or even 70° C. are allowed. With this robust enzyme systems it is possible to process hardstock fats, which have melting points higher than 30° C.–40° C., a range in which most aqueous lipase preparations have their maximum processing temperature.

The immobilized enzymes according to the invention may be employed in batch-wise processing as well as in continuous mode processing. The size of the solid enzyme coated particles should be large enough for allowing separation by centrifugation and is at least 0.1 μm, preferably at least 1 μm and more preferably 5–15 μm.

The invention further comprises processes catalyzed by an immobilized amphiphilic enzyme according to the invention. To such processes belong the hydrolysis either of triglycerides with a lipase or of phospholipids with a phospholipase, lipase catalyzed re-esterification of hydrolized triglycerides (de-acidification) or a combination of processes such as interesterification.

Interesterification processes may involve mono-, di- or triglycerides, in which, under the catalytic action of a lipase, fatty acid groups are exchanged on a glycerol backbone.

The enzymatic de-acidification of a triglyceride oil involves the catalytic action of a lipase where fatty acids and mono- or diglycerides present in the oil are esterified.

According to another embodiment the invention comprises a process for the removal of phospholipids from triglyceride oil (degumming) which comprises the steps of:

a. mixing a triglyceride oil containing phospholipids with a preparation containing a proper phospholipase, b. hydrolysing phospholipids to lysophospholipids, c. separating the hydrolysed phospholipids from the oil, characterized in that the phospholipase preparation is an immobilized enzyme according to the present invention. From the several phospholipases which are known and available the one is chosen which is most appropriate for the desired type of hydrolysis.

For the preparation of the immobilized phospholipase a phospholipid free hydrophobic phase should be used. After separation of a ready immobilized phospholipase it can be added to a phospholipid containing oil without harm for the enzyme preparation.

The in-situ immobilized enzyme is easily separated from a reaction batch by filtration, but preferably by centrifugation whereafter it can be re-used many times.

For re-use of an immobilized lipase no water needs to be added to a subsequent batch. The water dissolved in the triglyceride oil to be interesterified is sufficient for the initial hydrolysis step.

Figure 3:
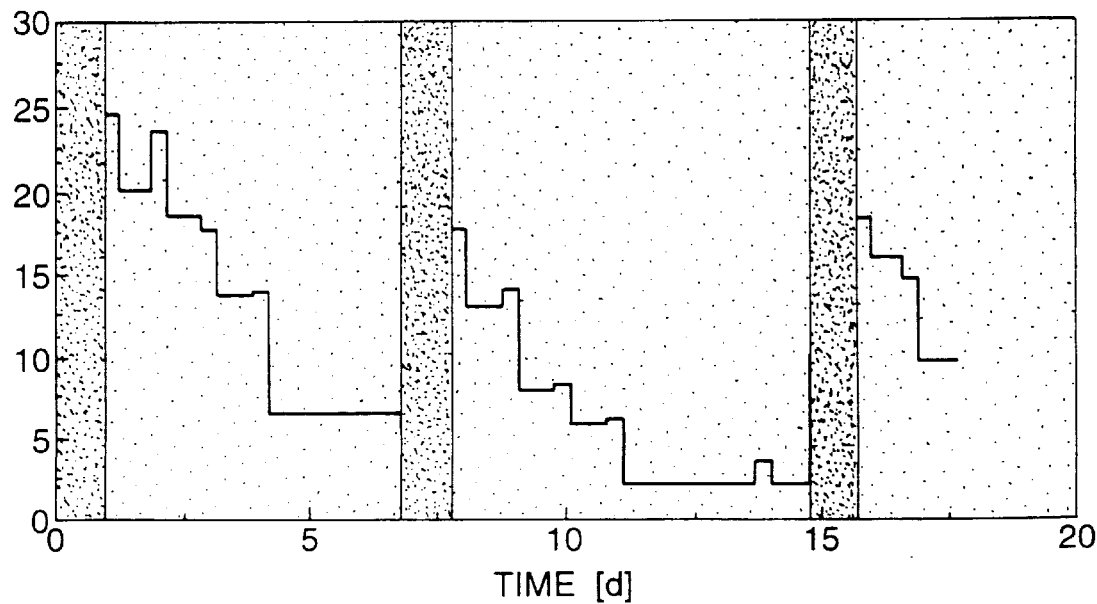
FIG. 3 shows for lipase obtained from *Humicola lanuginosa* and utilized in a subsequent series of interesterification batches, the activity (gram converted oil per gram enzyme per hour) as a function of time (days).

Optionally, any re-use of the enzyme may be preceded by a re-activation treatment: instead of separating the used immobilized enzyme from the hydrophobic phase, water, preferably 5–10 wt. %, is added and dispersed into the hydrophobic phase with the effect that the enzyme together with its carrier material dissolves in the water droplets. The enzyme again migrates to and accumulates in the water/oil interface. When the water is removed, as described before, the droplets by desiccation shrink and the carrier material again separates as solid matter. When the water is progressively disappearing from the desiccating droplets, the separated carrier material finally becomes coated by the enzyme. The re-immobilization results in a restoration, at least partially, of enzyme activity. This re-activation by re-immobilisation may be re-iterated again and again and provides a prolonged use of enzyme and carrier substance. FIG. 3 shows the re-use of an immobilized lipase enzyme in consecutive batches. The gradual decrease of enzyme activity is partially mended by re-immobilization using the same enzyme and the same carrier material (shaded areas). Optionally, enzyme damaged or spent during the process is compensated by adding some fresh enzyme preparation. The ongoing re-use of materials, additionally to the cheap source of enzyme in non-purified form, the absence of expensive carrier material and the high activity of the immobilized enzyme, greatly economizes on expensive catalyst. In the same time waste problems related to the disposal of spent enzyme material are absent. Such advantageous features are unique and not described for enzymes immobilized according to the prior art.

The invention is elucidated by the following examples:

GENERAL

Lipozyme™ 10000 L solution is a crude fermentation liquid freed from microorganisms which contains *Rhizomucor miehei* lipase (ex NOVO) and which has a lipase activity of 10 kLU/ml.

A purified form of a lipase is marketed by NOVO under the name Lipozyme IM™ or Lipozyme Immobilized on Duolite™. The activity is 70 kLU/gram powder.

Duolite™ is a weak anion exchange resin, which is suitable for enzyme immobilisation.

One lipase unit (LU) is defined as the amount of enzyme which liberates one micromole butyric acid per minute from an emulsified tributyrin substrate (at pH 7.0 and 30° C.).

In order to monitor the progress of the process in the following examples, oil samples were taken at time intervals. The samples, taken from the reaction medium with a needle, were heated above 85° C. in a 2 ml glass sample tube in order to deactivate the enzymes.

Free fatty acid content was determined by dissolving about 0.5 g of homogenised oil in 50 ml of a neutral solvent, comprising equal volumes of ethanol (96%) and diethyl ether (p.a.) and titrating it with a 0.1 mole/l sodium hydroxide solution, using phenolphtalein as indicator. The free fatty acid (FFA) content follows from:

$$\%FFa = V.M. \cdot 282/W \cdot 1000 \cdot 0.100\%$$

where:

V=titrated volume (ml)

W=weight of the oil sample (g)

M=molarity of the NaOH solution

282=average molecular weight of fatty acids.

The conversion degree follows from the following equations:

$$k = -\ln(1-x) * M/W \cdot t$$

where k: catalyst activity (g oil/g catalyst per h)

M: oil mass (g)

W: mass of catalyst (g enzyme preparation)

x: degree of conversion defined as t: cycle time (h)

$$x = \Sigma CN_0 - \Sigma CN_i / \Sigma CN_e - \Sigma CN_i$$

ΣCN represents the sum of the values of a range of carbon numbers selected for the specific process where the subscripts (o, i, e) refer to the reactor outlet at any moment in time (o), to the inlet (i) and to the equilibrium (e) distributions, respectively. The carbon number values are obtained by Gas Liquid Chromatography (GLC) sample analysis. For the HOSF/MCT interesterification the values of CN's 34–46 are selected and for the POs/PKs systems interesterification the values of CN's 44–46 are selected for calculating the degree of conversion.

EXAMPLE 1

COMPARISON OF IN-SITU IMMOBILIZED LIPASE AND TRADITIONALLY IMMOBILIZED LIPASE FOR INTERESTERIFICATION USE

A batch reactor, provided with a stirrer and a water jacket, was filled with a mixture of 131.5 g of medium chain triglycerides (MCT) and 229.0 g of high oleic sunflower oil (HOSF) for interesterification. 95% of the fatty acids of the MCT were C8–C10 fatty acids and 5% other acids.

The MCT/HOSF mixture was heated to 35° C. Under continuous stirring the oil was mixed with 5 wt. % of water, resulting in a W/O-emulsion. To the emulsion was added so much of a Lipozyme™ 10000 L solution, that the emulsion contained 165 LU activity per gram oil. Severe stirring produced a fine dispersion having a large oil and water interface.

The hydrolysis of the triglyceride molecules started after the aqueous phase addition and was continued at 35° C. until the 30% FFA level was attained.

By lowering the pressure to 6 mbar the water was evaporated causing the lipase to be deposited and immobilized on the dried fermentation residues.

Re-esterification started when the water was removed from the system and the temperature was raised to 50° C. FIG. 1 (lines with light dots) shows that after 50 hours of re-esterification the FFA content has dropped from about 30 wt. % to about 4 wt. %. The conversion degree of triglycerides reached nearly 80%.

In an equal way a comparison batch was prepared and processed but employing Lipozyme IM™ lipase traditionally immobilized on Duolite™. When adding lipase in an amount that the oil was given a lipase activity of 165 LU per gram oil the hydrolysis process started. Only 50 hours later the FFA content had reached the 24% level. Vacuum was applied, water was removed from the system and re-esterification started.

FIG. 1 (lines with heavy dots) shows the performance of the comparison batch.

The in-situ immobilized lipase of the invention shows a fast rate of hydrolysis and after the removal of water, a quick FFA reduction with a high conversion degree. Contrary to this, the process using the traditionally immobilized lipase shows a very low rate of hydrolysis and a low rate of FFA re-esterification, both of which resulted in a correspondingly low conversion degree.

EXAMPLE 2

COMPARISON OF IN-SITU IMMOBILIZED LIPASE AND TRADITIONALLY IMMOBILIZED LIPASE FOR DE-ACIDIFICATION USE

Figure 2:
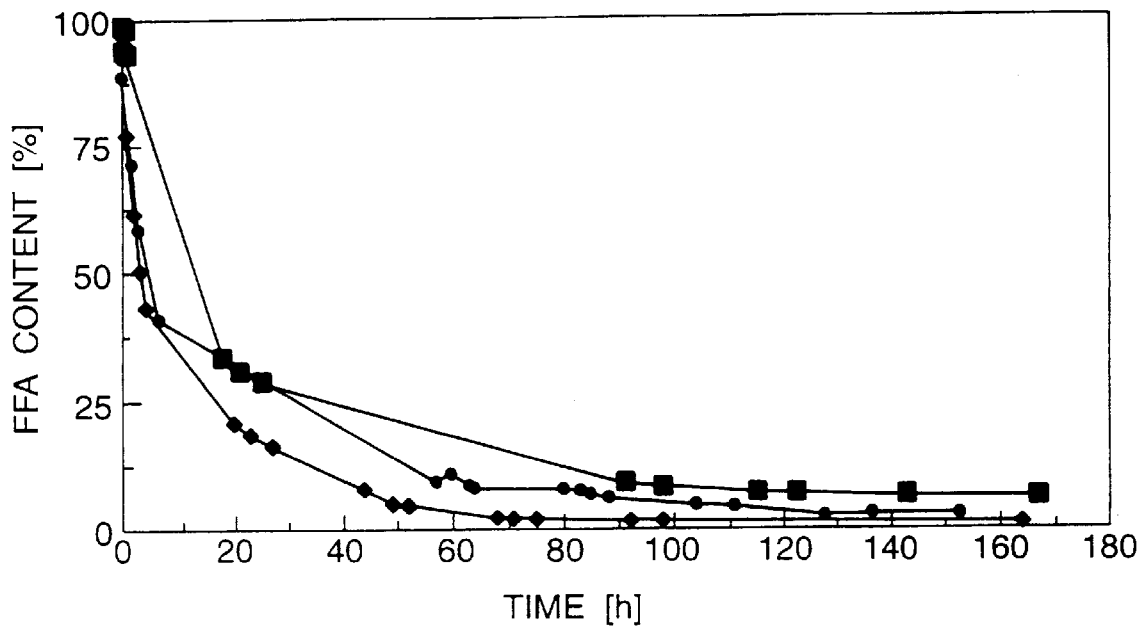
FIG. 2 is a diagram showing the free fatty acid content in the de-acidification of three mixtures of oleic acid and glycerol in the presence of immobilized lipase, comparing 1. Lypozyme™ 10000 L lipase (165 LU/g oil) in-situ immobilized according to the invention (indicated by a ● dotted line), 2. Lypozyme™ lipase (1750 LU/g oil) traditionally immobilized on Duolite™ (indicated by a ■ dotted line) and 3. Lypozyme™ lipase (3500 LU/g oil) traditionally immobilized on Duolite™ (indicated by a ♦ dotted line).

FIG. 2 is a diagram showing the free fatty acid content in the de-acidification of a mixture of oleic acid and glycerol in the presence of immobilized lipase, comparing lipase in-situ immobilized and lipase traditionally immobilized on Duolite™.

In a batch reactor 165.3 g of oleic acid and 18.0 g of glycerol were mixed and heated to 35° C. under constant stirring. The oil was prepared with 165 LU activity per gram oil employing an in-situ immobilized lipase prepared with Lipozyme™ 10000 L solution. The batch initially contained 7 g of molecular sieves and nitrogen was continuously conducted through the oil to strip the water.

After 83 hours of reaction a further 5 g of molecular sieves were added to the batch. See 0 dotted line of FIG. 2.

In an equal way two comparison batches were prepared and processed, but Lipozyme IM™ lipase which was traditionally immobilized on Duolite™ was used. One batch contained 1750 LU/g oil which in FIG. 2 is indicated by a ■ dotted line and the other batch contained 3500 LU/g oil indicated by a ♦ dotted line.

With the in-situ immobilized lipase an initial esterification rate of 7.5% FFA reduction/hour was attained as well as a total reduction of the FFA content from 88.4% to 3.3% in 150 hours. The initial esterification rates using traditionally immobilized lipases were 7.4% and 12.5% FFA reduction/hour for the low and the high concentration respectively. With the high lipase concentration a total reduction of the FFA content to 2.3% in 70 hours was attained.

Although the three de-acidification processes proceeded at comparable rates, the batch containing an in-situ immobilized lipase system needed only a fraction of the lipase activity both other batches used for the same performance.

What is claimed is:

1. A process for the immobilization of a lipase, comprising a. selecting a lipase for immobilization,
   b. preparing an emulsion comprising a continuous hydrophobic phase and a dispersed aqueous phase in which aqueous phase are dissolved the lipase and material suitable to act as carrier for the lipase when the next step is carried out, and
   c. removing water from the dispersed phase until this phase turns into solid lipase coated particles.

2. The process according to claim 1, wherein the lipase is obtained from *Rhizomucor miehei, Humicola lanuginosa* or *Rhizopus niveus*.

3. The process according to claim 1 wherein the aqueous phase comprises a fermentation liquid.

4. The process according to claim 1 wherein the hydrophobic phase is an edible triglyceride oil.

5. The process according to claim 1 wherein the carrier material is selected form the group consisting of sugars, starch, dextran, water soluble cellulose derivatives and fermentation residues.

6. The process according to claim 1 wherein the hydrophobic phase contains a substance to be processed which is selected form the group consisting of triglycerides, diglycerides, monoglycerides, glycerol, phospholipids and fatty acids.

7. The process according to claim 1 wherein the lipase as well as the carrier substance to be dissolved in the aqueous phase comprises immobilized lipase particles.

8. The process of claim 1 wherein the lipase is a phospholipase.

9. A process catalyzed by a lipase, comprising adding the lipase to reactants, wherein the lipase is an immobilized lipase prepared according to the process of claim 1.

10. A process for the interesterification of mono-, di- or triglycerides, in which, under the catalytic action of a lipase, fatty acid groups are exchanged on a glycerol backbone, wherein the lipase is an immobilized lipase prepared according to the process of claim 1.

11. A process for the enzymatic de-acidification of a triglyceride oil, where under the catalytic action of a lipase, fatty acid are esterified with mono- or diglycerides, comprising adding the lipase to the oil and wherein the lipase is an immobilized lipase prepared according to the process of claim 1.

12. A process for the removal of phospholipids from triglyceride oil comprising the steps:

a. mixing a triglyceride oil containing phospholipids with a preparation containing a phospholipase,
   b. hydrolysing the phospholipids to lysophospholipids,
   c. separating the hydrolysed phospholipids from the oil, wherein the phospholipase is an immobilized phospholipase prepared according to the process of claim 8.

* * * * *